United States Patent [19]

Steffen et al.

[11] Patent Number: 4,649,155
[45] Date of Patent: Mar. 10, 1987

[54] INJECTABLE SOLUTIONS

[75] Inventors: Hans Steffen, Arisdorf; Alberto Ferro, Riehen, both of Switzerland

[73] Assignee: Hoffmann-La Roche Inc., Nutley, N.J.

[21] Appl. No.: 631,264

[22] Filed: Jul. 16, 1984

[30] Foreign Application Priority Data

Jul. 22, 1983 [CH] Switzerland ......................... 4029/83
Jun. 6, 1984 [CH] Switzerland ......................... 2747/84

[51] Int. Cl.$^4$ ........................................... A61K 31/355
[52] U.S. Cl. ..................................... 514/458; 514/975
[58] Field of Search ......................... 514/78, 458, 975

[56] References Cited

U.S. PATENT DOCUMENTS

| | | | |
|---|---|---|---|
| 3,197,368 | 7/1965 | Lappe et al. | 424/199 |
| 3,993,756 | 11/1976 | Kaneda et al. | 424/195 |
| 4,005,190 | 1/1977 | Mader et al. | 424/199 |
| 4,252,793 | 2/1981 | Altman | 424/199 |
| 4,372,949 | 2/1983 | Kodama et al. | 424/199 |
| 4,486,417 | 12/1984 | Sugimoto et al. | 424/180 |

OTHER PUBLICATIONS

Chem. Abst. 90(19) 147314(x) (1979)–Cushley et al.
Chem. Abst. 95: 138633(b) (1981)–Teikoku Chem. Indust Co.
Chem. Abst. 98: 8191(g) (1983)–Nippon Shinyaku Co.
Chem. Abst. 98 95644(y) (1983)–Solisch et al.
Chem Abst. 99 52184(b) & 52185(c) (1983)–List et al.
Chem. Abst. 99 193,488r (1983)–Q. P. Corp.
Chem. Abst. 100 145,017(d) (1984)–Eisai Co.
Chem. Abst. 101 157,687(f) (1984)–Eisai Co.

*Primary Examiner*—Douglas W. Robinson
*Attorney, Agent, or Firm*—Jon S. Saxe; Bernard S. Leon; George M. Gould

[57] ABSTRACT

Aqueous vitamin E solutions useful for parenteral adminstration are disclosed. The solution comprises phospholipid-cholanic acid mixed micelles in which the molar ratio of phospholipid: cholanic acid is about 0.2–0.9:1 and about 100 g or more of vitamin E per mol of phospholipid.

4 Claims, No Drawings

INJECTABLE SOLUTIONS

BACKGROUND OF THE INVENTION

Heretofore, it was known that vitamin E can be dissolved in mixed micelles of cholanic acids and lecithins. However, these known solutions contained only small amounts of vitamin E. For example, in U.S. Pat. No. 3,197,368 there are described micelle solutions of lecithins and cholanic acids which can contain up to 2% of vitamin E ($\alpha$-tocopherol) based on the amount of lecithin. In German Auslegeschrift No. 2,433,173 there are described micelle solutions of phospholipids and glycocholic acid which contain 10 mg of vitamin E and 5 g of phospholipid per liter of solution.

There exists a need to make available substantially more concentrated solutions of vitamin E which would be useful in the preparation of injectable solution.

It has now been found that more concentrated solutions of vitamin E than heretofore reported can be prepared by employing certain molar ratios of phospholipid and cholanic acid.

SUMMARY OF THE INVENTION

The present invention relates to aqueous solutions of vitamin E useful in the preparation of injectable solutions. The aqueous solutions comprise a molar ratio of phospholipid to cholanic acid of about 0.2–0.9:1 and contain at least about 100 g of vitamin E per mol of phospholipid. This invention also relates to lyophilizates of the vitamin E containing solutions and to processes for preparing such solutions.

DETAILED DESCRIPTION OF THE INVENTION

This invention is directed to aqueous vitamin E solutions useful in the preparation of injectable solutions. The aqueous vitamin E solutions of the present invention comprise vitamin E, a phospholipid and a cholanic acid or salt thereof, wherein the molar ratio of phospholipid: cholanic acid is about 0.2–0.9:1 and the solution contains at least about 100 g of vitamin E per mol of phospholipid; and lyophilizates thereof. A preferred ratio of phospholipid: cholanic acid is about 0.25–0.5:1.

Cholanic acids which can be utilized in the solutions of the present invention are trihydroxycholanic acids such as cholic acid, glycocholic acid and taurocholic acid; dihydroxycholanic acids such as deoxycholic acid, glycodeoxycholic acid, taurodeoxycholic acid, chenodeoxycholic acid, glycochenodeoxycholic acid and taurochenodeoxycholic acid. Glycocholic acid is preferred. Cholanic acid salts are preferably alkali salts such as the sodium salt.

The phospholipids useful in the present invention are phosphatides such as phosphatidylcholines, glycerine ether phosphatides, phosphatidylethanolamine, phosphatidylinositol, phosphatidylserine, plasmologens or sphingomyelins. Phosphatidylcholines such as soya lecithin and egg lecithin are preferred. The term "vitamin E" is intended to embrace optically active and recemic vitamin E ($\alpha$-tocopherol).

The solutions of this invention can contain isotonizing additives in order to make them suitable for injection purposes. Examples of isotonizing additives include physiological sodium choloride and glucose solution, Tris buffer, phosphate buffer, citrate buffer, glycine buffer, citrate-phosphate mixed buffer and the like. The osmotic pressure of the injectable solutions in accordance with the invention should correspond approximately to that of the blood, i.e. to about 300 mOsm, but can vary within certain limits.

The solutions of this invention can also contain other additives. Examples of such additives include preserving agents and stabilizers, as well as other pharmaceutically active substances, e.g. other vitamins such as vitamin A, D, biotin, vitamins of the B group and vitamin C. In order to improve the stability, the solutions in accordance with the invention can contain e.g. ethanol.

The solutions of this invention can be prepared by known procedures for preparation of mixed micelle solutions. For example the phospholipid, the cholanic acid or salt therof and vitamin E can be dissolved in an organic solvent. After evaporating off the organic solvent, the water and, if desired, isotonizing additives and further ingredients are added. Organic solvents which can be used in the process are those in which the components to be dissolved are sufficiently soluble such as e.g. lower alkanols, especially ethanol.

A preferred process comprises suspending a cholanic acid, preferably glycocholic acid, in an ethanolic solution of vitamin E and lecithin and thereafter adding an amount of base, e.g. sodium hydroxide, which is required to convert the cholanic acid into a salt. The amount of ethanol is conveniently about 6–8 percent (%) by weight based on the total volume of the solution.

The resulting solution can be sterilized and, if desired, lyophilized.

Solutions suitable for injection can be reconstituted from water or isotonic salt solution. The invention is illustrated in more detail by the following Examples:

EXAMPLE 1

1.8 ml of a 10 percent by weight methanolic solution of d,l-$\alpha$-tocopherol, 0.76 ml of a 25 percent by weight ethanolic solution of PHOSPHOLIPON 100 (soya lecithin) and 3.9 ml of a 10 percent by weight methanolic sodium glycocholate solution are mixed together. The solvents are removed at 40° C. and the residue is treated with 3.24 ml of water and stirred to afford a clear solution. The solution is filtered sterile and filled into ampoules which are sterilized at 120° C. for 20 minutes.

EXAMPLE 2

50.0 mg of d,l-$\alpha$-tocopherol are dissolved in 70.0 mg of ethanol. 53.4 mg of lecithin are then dissolved in the resulting solution. 88.5 mg of glycocholic acid are carefully suspended in this solution. Thereafter, 506.6 $\mu$l of 1.5% (wt./vol) of sodium hydroxide solution are added and the mixture is stirred until a clear solution is obtained. The pH of the resulting solution is adjusted to pH 6 by the addition of 1N hydrochloric acid and made up to 1.0 ml with water for injection.

WE CLAIM:

1. An injectable aqueous micellar solution comprising vitamin E, a phospholipid and a cholanic acid or salt thereof, wherein the molar ratio phospholipid: cholanic acid is about 0.2–0.9:1 and the solution contains at least about 100 g of vitamin E per mol of phospholipid; or lyophilizates thereof.

2. The solution according to claim 1, wherein the molar ratio phospholipid: cholanic acid is about 0.25–0.5:1.

3. The solution according to claim 2, which contain about 10–50 g of vitamin E per liter.

4. The solution according to claim 1, which contain 6–8 percent by weight of ethanol based on the total volume.

* * * * *